US006624178B2

(12) United States Patent
Sankaranarayanan

(10) Patent No.: US 6,624,178 B2
(45) Date of Patent: *Sep. 23, 2003

(54) COMPOUNDS FOR THE MANAGEMENT OF AGING-RELATED AND DIABETIC VASCULAR COMPLICATIONS, PROCESS FOR THEIR PREPARATION AND THERAPEUTIC USES THEREOF

(75) Inventor: Alangudi Sankaranarayanan, Gujarat State (IN)

(73) Assignee: Torrent Pharmaceuticals Ltd., Gujarat (IN)

( * ) Notice: Subject to any disclaimer, the term of this patent is extended or adjusted under 35 U.S.C. 154(b) by 0 days.

This patent is subject to a terminal disclaimer.

(21) Appl. No.: 10/214,704

(22) Filed: Aug. 9, 2002

(65) Prior Publication Data

US 2003/0092744 A1 May 15, 2003

Related U.S. Application Data

(60) Division of application No. 09/598,410, filed on Jun. 21, 2000, now Pat. No. 6,462,057, which is a continuation-in-part of application No. PCT/IB99/01683, filed on Oct. 15, 1999.

(30) Foreign Application Priority Data

Oct. 6, 1999 (IN) .................................................. 828/99

(51) Int. Cl.[7] ...................... A61K 31/444; C07D 409/14
(52) U.S. Cl. ........................ 514/333; 546/256; 546/262; 546/263; 546/280.4; 546/324; 546/347; 514/336; 514/354; 514/356; 514/358
(58) Field of Search ................................. 514/333, 336, 514/354, 356, 358; 546/256, 262, 263, 280.4, 324, 347

(56) References Cited

U.S. PATENT DOCUMENTS

| 4,758,583 A | 7/1988 | Cerami et al. |
|---|---|---|
| 5,137,916 A | 8/1992 | Ulrich et al. |
| 5,272,176 A | 12/1993 | Ulrich et al. |
| 5,656,261 A | 8/1997 | Cerami et al. |
| 5,853,703 A | 12/1998 | Cerami et al. |
| 6,462,057 B1 * | 10/2002 | Sankaranarayanan ....... 514/336 |

FOREIGN PATENT DOCUMENTS

GB 822351 A 10/1959

OTHER PUBLICATIONS

Beisswenger et al, *Diabetes*, 11:824–829 (1995).
Beisswenger et al, *J. Clin. Invest.*, 92:212–217 (1993).
Anderson et al, *J. Clin. Invest.*, 92:3045–3052 (1993).
Makita et al, *New England J. of Med.*, 325(12):836–842 (1991).
Yamauchi et al, *Diabetes Res. Clin. Pract.*, 34(3):127–133 (1997) (Abstract only).

Ellis et al, *Metabolism*, 40(10):1016–1019 (1991) (Abstract only).
Nakamura et al, *Diabetes*, 46(5):895–899 (1997).
Soulis–Liparota et al, *Diabetes*, 40:1328–1334 (1991).
Chibber et al, *Diabetologia*, 40(2):156–164 (1997).
Hirata et al, *Biochem. Biophys. Res. Commun.*, 236(3):712–715 (1997).
Murata et al, *Diabetologia*, 40(7):764–769 (1997).
Clements Jr. et al, *J. Diabetes Complications*, 12(1):28–33 (1998) (Abstract only).
Hammes et al, *Proc. Natl. Acad. Sci., USA*, 88:11555–11558 (1991) (with 1 page correction).
Hammes et al, *Diabetologia*, 37(1):32–35 (1994).
Roufail et al, *Diabetologia*, 41(12):1419–1425 (1998).
Kihara et al, *Proc. Natl. Acad. Sci., USA*, 88:6107–6111 (1991).
Miyauchi et al, *Eur. J. Endocrinol.*, 134(4):467–473 (1996) (Abstract only).
Yagihashi et al, *Diabetes*, 41:47–52 (1992).
Ritthaler et al, *Nephrol Dial Transplant*, 10(9):1662–1667 (1995).
Amore et al, *Kidney International*, 51:27–35 (1997).
Bierhaus et al, *Circulation*, 96(7):2262–2271 (1997).
Bierhaus et al, *Diabetes*, 46:1481–1490 (1997).
Kunt et al, *Exp. Clin. Endocrinol Diabetes*, 106:183–188 (1998).
Kunt et al, *Int. J. Mol. Med.*, 2(4):455–460 (1998) (Abstract only).
Vlassara et al, *Molecular Medicine*, 1(4):447–456 (1995).
Kyurkchiev et al, *Cell Mol Life Sci.*, 53(11–12):911–916 (1997) (Abstract only).
Yamagishi et al, *Diabetologia*, 41(12):1435–1441 (1998).
Hogan et al, *J. Clin. Invest.*, 90(3):1110–1115 (1992).
Tezuka et al, *Biochem Biophys. Res. Commun.*, 193(2):674–680 (1993) (Abstract only).

(List continued on next page.)

*Primary Examiner*—Charanjit S. Aulakh
(74) *Attorney, Agent, or Firm*—Sughrue Mion, PLLC

(57) ABSTRACT

The invention discloses novel compounds of the pyridinium series useful for the management of diabetes and aging-related vascular complications, including kidney disease, nerve damage, atherosclerosis, retinopathy, dermatological disorders and discoloration of teeth, by breaking preformed AGE, of the general formula I, or pharmaceutically acceptable salts thereof,

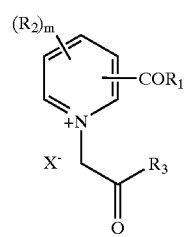

wherein, $R_1$, $R_2$, $R_3$, X and m are as defined in the specification.

23 Claims, No Drawings

OTHER PUBLICATIONS

Bonnardel–Phu et al, *Diabetes*, 48:2052–2058 (1999).
Vlassara et al, *Proc. Natl. Acad. Sci., USA*, 89:12043–12047 (1992).
Bucala, *Diabetes Res. Clin. Pract.*, 30(Suppl):123–130 (1996) (Abstract only).
Kirstein et al, *Proc. Natl. Acad. Sci., USA*, 87:9010–9014 (1990).
Wolffenbuttel et al, *Proc. Natl. Acad. Sci., USA*, 95:4630–4634 (1998).
Aronson et al, *J. Am. Coll Cardiol.*, 27(3):528–535 (1996) (Abstract only).
Seftel et al, *Urology*, 50(6):1016–1026 (1997) (Abstract only).
Vitek et al, *Proc. Natl. Acad. Sci., USA*, 91:4766–4770 (1994).
Li et al, *Proc. Natl. Acad. Sci., USA*, 93:3902–3907 (1996).
Nordbo, *J. Dent. Res.*, 58(4):1429 (1979) (Abstract only).
Nakayama et al, *Biochem. Biophys. Res. Comm.*, 162(2):740–745 (1989).
Araki et al, *J. Biol. Chem.*, 267(15):10211–10214 (1992).
Horiuchi et al, *J. Biol. Chem.*, 266(12):7329–7331 (1991).
Booth et al, *Biochem. Biophys. Res. Comm.*, 220(Art. No. 0366):113–119 (1996).
Brownlee, *Annu. Review Med.*, 46:223–234 (1995).
Shikata et al, *J. Diabetes Complic.*, 9(4):269–271 (1995).
Kenichi Shikata et al, Journal of Diabetes and its complications 1995:9:269–271.
Sara Vasan et al, Nature, vol. 382, Jul. 18, 1996, 275–278.
M. Brownlee et al Science Jun. 1986, 232:1629–32.
A. Ceriello, Diab. Nurt. Metab. 12:42–46, 1999.
Horiuchi S et al, The Journal of Biological Chemistry 1991, 226:7329–7332.
Wolffenbuttel, B.H.R. et al Proc. Natl. Acad. Sci. USA, Apr. 1998:4630–4634.
Mohammed Asif et al, PNAS Mar. 14, 2000, vol. 97, No. 6, 2809–2813.
Raj D S et al, Am J Kidney Dis Mar. 2000 35(3):365–80.
J. Shashi et al, Indian drugs, 1995, 32(7) pp. 317–319 (XP000909803).
Tiwari, S.S. et al, J. Indian Chem Soc, 1975 52(2) 166–7 (XP000909760).
Mocanu, G. et al. S.T.P. Pharma Sciences 1994, 4(4) 287–291 (XP000909810).
Sarel, Shalom et al J. Med. Chem. 1999, 42(2) 242–248 (XP000910109).
Demchenko, A.M. et al, Chemistry of Heterocyclic compounds 1997, 33(10), 1191–1195 (XP000909851).
Onodera, Akira et al, Chemical Abstracts, vol. 120, No. 8, Feb. 21, 1994, abstract No. 90688 (XP002139440).
Pandey V.K. et al, Indian drugs, 1983, 20(12) 492–4 (XP000909902).
Maksimovic, Matez et al, Chemical Abstracts, vol. 96 No. 13, Mar. 29, 1982 Abstract No. 99045 (XP002139441).
Binenfeld, Zlatko et al Acta Pharm. Jugosl 1981, 31(1), 5–15 (XP000909901).
Ergenc, Nedime Chemical Abstracts vol. 65, No. 6, Sep. 12, 1966, abstract No. 8891f (XP002139442).
Kao, Yee–Shang et al, Chemical Abstracts vol. 52, No. 3, 1958 abstracts No. 12860f (XP002139443).
PCT Search Report of Corresponding PCT Application No. PCT/IB99/01683 dated Jul. 10, 2000.
International Preliminary Examination Report for PCT/IB99/01683 dated Dec. 21, 2001.
Complete Chinese Language Reference of Kao Yee–Shang et al, Chemical Abstracts vol. 52, No. 3, 1958.
Registry Compound No. 220468–94–0.

* cited by examiner

COMPOUNDS FOR THE MANAGEMENT OF AGING-RELATED AND DIABETIC VASCULAR COMPLICATIONS, PROCESS FOR THEIR PREPARATION AND THERAPEUTIC USES THEREOF

CROSS-REFERENCE TO RELATED APPLICATIONS

This application is a divisional of application Ser. No. 09/598,410 filed Jun. 21, 2000 now U.S. Pat. No. 6,462,057, which is a continuation-in-part of International Application No. PCT/IB99/01683 filed Oct. 15, 1999, the disclosures of which are incorporated herein by reference.

BACKGROUND OF THE INVENTION

1. Field of the Invention

The present invention relates to a new class of compounds of pyridinium series and to their use in treatment of diabetes and related illnesses. More particularly the invention relates to compounds of this series, methods for their preparation, pharmaceutical composition containing these compounds and their use in the treatment of complications of diabetes mellitus. The compounds of this series exhibit AGE breaking activity, which is essential for the treatment of diabetic and aging-related complications including kidney disease, nerve damage, atherosclerosis, retinopathy and dermatological conditions. The invention also extends to the method of reversing the discoloration of teeth resulting from nonenzymatic browning in the oral cavity which comprises administration of an amount effective to reverse pre-formed advanced glycosylation crosslinks.

2. Description of the Prior Art

Maillard in 1912 found that reducing sugars, such as glucose and ribose react with proteins to form brown pigments. Further studies have shown that this is an irreversible non-enzymatic reaction, which occurs in several natural systems including stored foodstuff. Maillard reaction occurs in two stages, early and advanced. Initially, proteins react with glucose to form stable Amadori products, which subsequently cross-links to form advanced glycation end products (AGE). In most cases, the formation of AGE also accompanies browning of the proteins and increase in the fluorescence.

In diabetes, where blood glucose level is significantly higher than normal, the reaction of glucose with several proteins such as haemoglobin, lens crystallin and collagen, gives rise to the formation of AGE, which in turn, is responsible for the complications associated with diabetes, such as nephropathy, microangiopathy, endothelial dysfunction and other organ dysfunctions. In addition, the activity of several growth factors, such as basic fibroblast growth factor, is also impaired. AGE products, unlike normal proteins in tissue, have a slower rate of turnover and replenishment. It has been reported that AGE products may in fact elicit a complex immunological reaction involving RAGE (Receptor for Advanced Glycation End Products) receptors and activation of several incompletely defined immunological processes. It has been documented that diabetes with evidence of microangiopathy and macroangiopathy also show evidence of oxidative stress, the mechanism of which has not been elucidated.

In vitro AGE formation can be studied in the laboratory by incubating reducing sugars, such as ribose or glucose with bovine serum albumin. AGE formation can be detected by increase in the fluorescence or increased cross reactivity with anti-AGE antibodies. The increase in fluorescence seems to precede formation of AGE specific antigenic epitopes. This increase in fluorescence is used to monitor the increased AGE formation in vitro (Brownlee M et al, Science 1986; 232:1629–1632). In addition to the increase in the fluorescence, one of the most important features of in vitro AGE formation is the formation of antigenic epitopes that are specific to AGE and not to the native proteins. Therefore, it is possible to raise antibodies against advanced glycation end products of one protein and use them to detect AGE formation in other proteins. This has served as an important analytical tool in AGE research.

Due to the clinical significance of AGE formation, many approaches are being used to diagnose, prevent, or revert AGE formation in the body. The formation of AGE could be inhibited by reacting with an early glycosylation product that results from the original reaction between the target protein and glucose. The inhibition was believed to take place as the reaction between the inhibitor and the early glycosylation product appeared to interrupt the subsequent reaction of the glycosylated protein with additional protein material to form the cross linked late stage product. Compounds like aminoguanidine act to inhibit AGE formation by such mechanism.

The formation of AGE on long-lived proteins is also associated with cross-linking of these proteins. The AGE derived protein cross-links have been shown to be cleaved by compounds like N-phenacyl thiazolium bromide (PTB), which reacts with and cleaves covalent, AGE derived protein cross links (Vasan et al. Nature 1996; 382: 275–278; U.S. Pat. No. 5,853,703, Date of Patent: Dec. 29, 1998). The mechanism of reducing the AGE content in tissues is expected to take place relatively rapidly, in contrast to aminoguanidine, which acts slowly by its very nature of mechanism of action. This current specification is related to compounds of pyridinium class, which break pre-formed AGE, like PTB, and in some cases even more effectively by than PTB.

SUMMARY OF THE INVENTION

The main objective of the present invention is to provide a new class of compounds of the pyridinium series which are useful for the management of diabetes and aging related vascular complications and particularly in the treatment of complications of diabetes mellitus and other aging related conditions including kidney disease, nerve damage, atherosclerosis, retinopathy and dermatological conditions. The invention also extends the method to reverse the discoloration of teeth resulting from nonenzymatic browning in the oral cavity which comprises administration of an amount effective to reverse the pre-formed advanced glycosylation crosslinks, etc.

Another object of the present invention is to provide compounds of the pyridinium series, which exhibit AGE breaking activities.

Yet another object of the present invention is to provide a method of preparation of compounds of the pyridinium series which exhibit AGE breaking activities.

Still another object of the invention is to provide pharmaceutical compositions with a new class of compounds of the pyridinium series according to the invention and their pharmaceutically acceptable salts in combination with suitable carriers, solvents, excepients, diluents and other media normally employed in preparing such compositions.

Still another object of the invention is to provide a method of treatment of a diabetic patient by administration of the compounds of the invention, either singly or in combination with drugs for anti-diabetic therapy, or pharmaceutically acceptable salts thereof in required dosage in admixture with pharmaceutically acceptable diluent, solvent, excepients, carriers or other media as may be appropriate for the purpose.

DETAILED DESCRIPTION OF THE INVENTION

The present invention provides for a new class of AGE breakers, of general formula I,

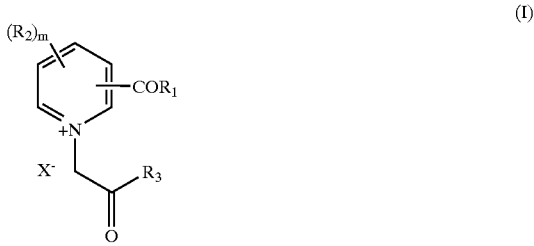

wherein
$R_1$ is —$R_4$-$R_5$ or —N($R_7$)N ($R_7$)$R_9$;
$R_4$ is selected from the group consisting of —N($R_7$)$R_6$O—, —N($R_7$)$R_6$N($R_7$)—, O$R_6$O, and —O$R_6$N($R_7$)—,
where $R_6$ is alkyl;
$R_5$ is selected from the group consisting of alkyl, aryl including heteroaryl, —CO$R_7$, SO$_2R_7$, —C(S)NH$R_7$, —C(NH)NH$R_7$, —CO$R_{10}$,

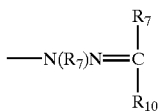

where $R_7$ is selected from the group consisting of H, alkyl and aryl including heteroaryl provided $R_7$ might be different for $R_1$ and $R_3$ in the same compound;
$R_2$ is selected from the group consisting of F, Cl, Br, I, O$R_7$, NO$_2$, alkyl, aryl including heteroaryl, formyl, acyl, C(O)N$R_7R_{10}$, C(O)O$R_7$, N$R_7R_{10}$, N=C($R_7$)($R_{10}$), S$R_7$, SO$_2$NH$_2$, SO$_2$ alkyl and SO$_2$aryl,
and m is 0, 1 or 2;
$R_3$ is selected from the group consisting of $R_7$, O$R_7$, N($R_7$)($R_{10}$), N=C($R_7$)($R_{10}$), N($R_7$)N($R_7$)($R_{10}$), N($R_7$)N=C($R_7$)($R_{10}$) and CH($R_7$)C(O)$R_8$
where $R_8$ is selected from the group consisting of $R_7$, O$R_7$ and N$R_7R_{10}$;
$R_9$ is selected from the group consisting of hydrogen, alkyl, aryl including heteroaryl, C(O)$R_{10}$, —SO$_2R_{10}$, —C(S)NH$R_{10}$, —C(NH)NH($R_{10}$) and —C(O)NH$R_{10}$,
$R_{10}$ is selected for the group consisting of H, alkyl or aryl including heteroaryl and in each case optionally different from substituent $R_{10}$, provided $R_{10}$ might be different for $R_1$ and $R_3$ in the same compound;
X is selected from group consisting of a halide ion, acetate ion, perchlorate ion, sulfonate ion, oxalate ion, citrate ion, tosylate ion, maleate ion, mesylate ion, carbonate ion, sulfite ion, phosphoric hydrogen ion, phosphonate ion, phosphate ion, BF$_4^-$ and PF$_6^-$;
with proviso that,
(i) when two alkyl groups are present on the same carbon or nitrogen, they are optionally linked together to form a cyclic structure and (ii) the nitrogen of heteroaryl ring of $R_{10}$, when present, is optionally quaternized with compound such as X—CH$_2$C(O)—$R_3$ As used herein, "alkyl" refers to an optionally substituted hydrocarbon group joined by single carbon-carbon bonds and having 1 to 8 carbon atoms joined together. The alkyl hydrocarbon group may be linear, branched or cyclic, saturated or unsaturated. The substituents are selected from F, Cl, Br, I, N, S, O and aryl. Preferably, no more than three substituents are present.

As used herein "aryl" refers to an optionally substituted aromatic group with at least one ring having a conjugated pi-electron system, containing up to two conjugated or fused ring systems. Aryl includes carbocyclic aryl, heterocyclic aryl and biaryl groups, all of which may be optionally substituted. The substituents are selected from F, Cl, Br, I, N, S, O and straight chain or branched $C_1$–$C_6$ hydrocarbon.

The novel compounds of the invention of general formula I having m as 0 and —CO$R_1$ at position 3 are listed in Table 1A and the novel compounds of the invention of general formula I having m as 0 and —CO$R_1$ at position 4 are listed in Table 1B. The following compounds suggested are by way of example alone of the representative compounds of the general formula I as defined above and in no way restrict the invention.

N,N'-Bis[3-carbonyl-1-(2-phenyl-2-oxoethyl)-pyridinium] hydrazine dibromide (compound 1):
N,N'-Bis[3-carbonyl-1-(2-ethoxy-2-oxoethyl)pyridinium] hydrazine dibromide (compound 2):
N,N'-Bis[3-carbonyl-1-(2-(2,4-dichlorophenyl)-2-oxoethyl) pyridinium]hydrazine dibromide (compound 3):
1-(2-Ethoxy-2-oxoethyl)-3-(2-(2-pyridyl) hydrazinocarbonyl)pyridinium bromide.hydrochloride (compound 4):
1-(2-Thien-2'-yl-2-oxoethyl)-3-(methanesulfonyl hydrazinocarbonyl)pyridinium bromide (compound 5):
N,N'-Bis[3-carbonyl-1-(2-thien-2'-yl-2-oxoethyl) pyridinium]hydrazine dibromide (compound 6):
1-(2-Ethoxy-2-oxoethyl)-3-(2-(benzoyloxy) ethylaminocarbonyl)pyridinium bromide (compound 7):
1-(2-(2,4-Dichlorophenyl)-2-oxoethyl)-3-(2-(benzoyloxy) ethylamino-carbonyl)pyridinium bromide (compound 8):
1-(2-Thien-2'-yl-2-oxoethyl)-3-(2-(2-pyridyl) hydrazinocarbonyl)pyridinium bromide (compound 9):
1-(2-Phenyl-2-oxoethyl)-3-(2-(2-pyridyl) hydrazinocarbonyl)pyridinium bromide (compound 10):
1-(2-Phenyl-2-oxoethyl)-3-(hydrazinocarbonyl)pyridinium bromide (compound 11).
1-(2-Phenyl-2-oxoethyl)-3-(methanesulfonyl hydrazinocarbonyl)pyridinium bromide (compound 12):
1-(2-Ethoxy-2-oxoethyl)-3-(methanesulfonyl hydrazinocarbonyl)pyridinium bromide (compound 13):
1-(2-Phenyl-2-oxoethyl)-3-(phenylsulfonylhydrazino carbonyl)pyridinium bromide (compound 14):
1-(2-Phenyl-2-oxoethyl)-2-chloro-3-(phenylsulfonylhydrazino carbonyl)pyridinium bromide (compound 15):
1-(2-Phenyl-2-oxoethyl)-3-(2-(acetoxy)ethyloxy carbonyl) pyridinium bromide (compound 16):
1-(2-Ethoxy -2-oxoethyl)-3-(2-(benzoyloxy)ethyloxy carbonyl)pyridinium bromide (compound 17):
1-(2-Thien-2'-yl-2-oxoethyl)-4-(2-(benzoyloxy) ethylaminocarbonyl)pyridinium bromide (compound 18):
1-(2-Ethoxy -2-oxoethyl)-4-(phenylsulfonyl hydrazino carbonyl)pyridinium bromide (compound 19):

1-(2-Phenylamino-2-oxoethyl)-4-(phenylsulfonyl hydrazino carbonyl)pyridinium chloride (compound 20):
1-(2-Ethoxy -2-oxoethyl)-3-(phenylsulfonyl hydrazino carbonyl)pyridinium bromide (compound 21):
1-(2-(2,4-Dichlorophenyl)-2-oxoethyl)-3-(2(methoxy) ethyloxycarbonyl)pyridinium bromide (compound 22):
1-(2-Phenylamino-2-oxoethyl)-3-((benzoyloxy) ethylaminocarbonyl)pyridinium chloride (compound 23):
1-(2-Thien-2'-yl-2-oxoethyl)-3-(phenylaminocarbonyl hydrazinocarbonyl)pyridinium bromide (compound 24):
1-(2-Phenyl-2-oxoethyl)-3-(2-(acetoxy) ethylaminocarbonyl)pyridinium bromide (compound 25):
1-(2-Phenylamino-2-oxoethyl)-3-(phenyl sulfonyl hydrazino carbonyl)pyridinium chloride (compound 26):
1-(2-Phenylamino-2-oxoethyl)-3-((4-methylphenyl) sulfonyl hydrazino carbonyl)pyridinium chloride (compound 27):
1-(2-Phenyl-2-oxoethyl)-3-(2-(benzoyloxy)ethyloxy carbonyl)pyridinium bromide (compound 28):
1-(2-Thien-2'-yl-oxoethyl)-3-(phenylcarbonyl hydrazino carbonyl)pyridinium bromide (compound 29):
1-(2-Ethoxy-2-oxoethyl)-3-((phenylmethyl)sulfonyl hydrazino carbonyl)pyridinium bromide (compound 30):
1-(2-Phenyl-2-oxoethyl)-3-((phenylmethyl)sulfonyl hydrazino carbonyl)pyridinium bromide (compound 31):

TABLE 1A

Representative Pyridinium derivatives
(having m as 0 and —$COR_1$ at position 3)

| Compound | —$R_1$ | —$R_2$ | —$R_3$ | —X |
|---|---|---|---|---|
| 1 | Structure (a) | — | Phenyl | Br |
| 2 | Structure (b) | — | Oet | Br |
| 3 | Structure (c) | — | 2,4-dichlorophenyl | Br |
| 4 | NHNH-(2-pyridyl) | — | OEt | Br |
| 5 | $NHNHSO_2CH_3$ | — | 2-thienyl | Br |
| 6 | Structure (d) | — | 2-thienyl | Br |
| 7 | $NHCH_2CH_2OCOPh$ | — | OEt | Br |
| 8 | $NHCH_2CH_2OCOPh$ | — | 2,4-dichlorophenyl | Br |
| 9 | NHNH-(2-pyridyl) | — | 2-thienyl | Br |
| 10 | NHNH-(2-pyridyl) | — | Phenyl | Br |
| 11 | $NHNH_2$ | — | Phenyl | Br |
| 12 | $NHNHSO_2CH_3$ | — | Phenyl | Br |
| 13 | $NHNHSO_2CH_3$ | — | OEt | Br |
| 14 | NHNH—$SO_2$phenyl | — | Phenyl | Br |
| 15 | NHNH—$SO_2$phenyl | 2-Cl | Phenyl | Br |
| 16 | $OCH_2CH_2OCOCH_3$ | — | Phenyl | Br |
| 17 | $OCH_2CH_2OCOPh$ | — | OEt | Br |
| 21 | —NHNH—$SO_2Ph$ | — | OEt | Br |
| 22 | —$OCH_2CH_2OCH_3$ | — | 2,4-dichlorophenyl | Br |
| 23 | —$NHCH_2CH_2OCOPh$ | — | NH phenyl | Cl |
| 24 | —NHNHCONHPh | — | 2-thienyl | Br |
| 25 | $NHCH_2CH_2OCOCH_3$ | — | Phenyl | Br |
| 26 | $NHNHSO_2Ph$ | — | NH phenyl | Cl |
| 27 | $NHNHSO_2Ph(4-CH_3)$ | — | NH phenyl | Cl |
| 28 | $OCH_2CH_2OCOPh$ | — | Phenyl | Br |
| 29 | —NHNHCOPh | — | 2-thienyl | Br |
| 30 | $NHNHSO_2CH_2Ph$ | — | OEt | Br |
| 31 | $NHNHSO_2CH_2Ph$ | — | Phenyl | Br |

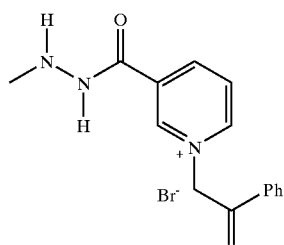

(a)

TABLE 1A-continued

Representative Pyridinium derivatives
(having m as 0 and —$COR_1$ at position 3)

| Compound | —$R_1$ | —$R_2$ | —$R_3$ | —X |
|---|---|---|---|---|

(b)

(c)

(d)

TABLE 1B

Representative Pyridinium derivatives
(having m as 0 and -$COR_1$ at position 4)

| Compound | —$R_1$ | —$R_2$ | —$R_3$ | —X |
|---|---|---|---|---|
| 18 | $NHCH_2CH_2OCOPh$ | — | 2-thienyl | Br |
| 19 | $NHNHSO_2Ph$ | — | OEt | Br |
| 20 | $NHNHSO_2Ph$ | — | NH phenyl | Cl |

According to the embodiment of the present invention, the present compounds are used for the treatment of diabetic complications, and aging related complications including kidney disease, nerve damage, atherosclerosis, retinopathy, dermatological conditions and colouration of teeth occurring due to the higher levels of preformed AGE. The increased levels of preformed AGE can be brought under control by breaking the AGE products using compounds mentioned in the invention.

The invention also provides a process for the preparation of novel compounds of the pyridinium series.

The said process for the preparation of compound 1, comprises, adding a solution of phenacyl bromide in iso-propanol to N,N'-bis-(nicotinyl)hydrazine dissolved in methanol, refluxing for six hours, cooling, filtering the precipitated solid, washing the solid with hot ethyl acetate and finally purifying the solid with 20 ml of methanol:ethyl acetate (3:1) to yield the desired compound.

Similarly, the other novel compounds of general formula I, are prepared from properly substituted pyridine derivatives followed by quarternization with appropriate reagent by refluxing in alcoholic solvents like, methanol, ethanol, propanol, etc and high boiling solvents like toluene or xylene etc, for 6–48 hrs. to give the desired compounds.

The in vitro AGE formation, studied in the laboratory, by incubating reducing sugar glucose, with protein bovine serum albumin, resulted in browning of solution and increase in the fluorescence. Fluorescence was used as the criteria to monitor the increased AGE formation.

EXAMPLE 1

AGE Breaker Activity has been Confirmed by the Screening Procedure as Mentioned Below:

Materials:
Bovine serum albumin (fraction V)(BSA)
Glucose, analytical grade
Phosphate buffered saline (PBS)

Equipment:
Microplate ELISA Reader—Spectramax Plus (Molecular Devices, USA)
Microplate washer, (Bio-Tec Instruments, USA)
pH meter Methods of Experiment: Elisa (Enzyme Linked Immunosorbent Assay)

160 mg/ml of protein, bovine serum albumin, BSA and 1.6M glucose sugar were dissolved in phosphate buffered saline, PBS. Sodium azide was added at 0.02% concentration as a preservative. The solution was filtered asceptically through a 0.22 μM filter and kept for aging at 37° C. for 16 weeks. After 16 weeks the solution was dialyzed against PBS, aliquoted and stored at −20° C.

To determine the AGE breaking activity, 10 μg/ml of the 16 weeks AGE-BSA was incubated with different concentrations of the test compounds at 37° C. for 24 hours and AGE breaking activity of the test compounds by ELISA was determined.

ELISA was performed as follows:
1. Different concentrations of 16 weeks AGE-BSA were coated on a microtitre plate as standard. Each concentration is coated in triplicates.
2. The test samples were coated on microtitre plate at a concentration of 5 ng. to 20 ng per well in triplicates.
3. The plate was incubated at 37° C. for one hour.
4. After incubation the plate was washed with PBST (PBS with 0.05% Tween 20).
5. Blocking with 5% skimmed milk in PBS at 37° C. for one hour was done.
6. The plate was washed with PBST.
7. Primary antibody against AGE-BSA was added and the plate is incubated at 37° C. for one hour.
8. The plate was washed with PBST
9. Secondary antibody anti rabbit HRPO (Horse-Radish Per Oxidase) conjugate was added and the plate is incubated at 37° C. for one hour.
10. The plate was washed with PBST.
11. Colour development with OPD (orthophenylenediamine dihydrochloride) and hydrogen peroxide was done.
12. OD (optical density) at (450 nm reading–620 nm reading) was measured after incubation at 37° C. for 15 minutes with Microplate ELISA Reader.

The breaker activity of the compounds were determined by the following formula:

$$\% \text{ Breaker activity} = \frac{OD_{450-620}Control - OD_{450-620}Test}{OD_{450-620}Control} \times 100$$

$OD_{450-620}$Control=Absorbance of 20 ng AGE-BSA after incubation at 37° C. for 24 hours without test compound
$OD_{450-620}$ Test=Absorbance of 20 ng AGE-BSA after incubation at 37° C. for 24 hours with required concentration of test compound Using specific examples, the % AGE breaking activity was calculated and recorded in Table 2.

TABLE 2

| Sample | Concentration | % Breakage |
|---|---|---|
| PTB | 10 mM | 27 |
|  | 20 mM | 47 |
| Compound 1 | 5 mM | 13 |
| Compound 4 | 10 mM | 30 |
| Compound 5 | 10 mM | 16 |
|  | 50 mM | 68 |
| Compound 6 | 5 mM | 53 |
| Compound 7 | 20 mM | 36 |
| Compound 16 | 10 mM | 16 |
| Compound 17 | 10 mM | 19 |
| Compound 22 | 10 mM | 13 |
|  | 25 mM | 41 |
| Compound 23 | 10 mM | 37 |
|  | 25 mM | 90 |

Hence compound 6 has significant AGE breaking activity i.e. a comparatively much superior potency vis-a-vis PTB.

The following examples give method of preparation of the specific novel compounds of the invention as given in Table 1. The following compounds suggested are by way of example alone and in no way restrict the invention.

EXAMPLE 2

Preparation of N,N'-bis[3-carbonyl-1-(2-phenyl-2-oxoethyl) pyridinium]hydrazine dibromide (Compound 1):

To a boiling solution of N, 2'-bis-(nicotinyl)hydrazine (1.21 g., 0.005 mol.) in methanol (20 ml.), a solution of phenacyl bromide (1.99 g., 0.01 mol.) in isopropanol (10 ml.) was added and the reaction mixture was refluxed for 6 hrs. The reaction mixture was concentrated under vacuum (~10 ml.) and filtered. The obtained residue was washed with hot ethylacetate and then the isolated solid was powdered. It was recrystallised from a mixture of methanol and ethylacetate (3:1, 20 ml) to afford a pale yellow solid.

Yield: 60%
m.p.: 260–262° C. (decomp.)
IR(KBr, cm$^{-1}$): 1696 and 1680
$^1$H NMR (DMSOd$_6$, 400 MHz) δ: 11.65(2H,s), 9.56(2H, s), 9.21–9.16(4H,m), 8.49–8.45 (2H,m), 8.08–8.05 (4H,d), 7.81–7.77(2H,m), 7.68–7.64 (4H,m), 6.58 (4H,s)
Mass (m/z): 479, 480

According to the above mentioned procedure the following compounds are synthesized by reacting the corresponding pyridine derivatives with appropriate reagents by refluxing in methanol, ethanol, propanol, toluene or xylene for 6–48 hrs. to get the desired compounds:

EXAMPLE 3

N,N'-Bis[3-carbonyl-1-(2-ethoxy-2-oxoethyl)pyridinium] hydrazine dibromide (Compound 2):

Yield: 47%
m.p.: 180–182° C. (decomp.)
IR(KBr, cm$^{-1}$): 1744, 1664
$^1$H NMR (DMSOd$_6$, 400 MHz) δ: 11.65 (2H,s), 9.62 (2H,s), 9.28–9.26 (2H,d), 9.17–9.15 (2H,d), 8.47–8.44 (2H, m), 5.77 (4H,s), 4.26 (4H,q), 1.27 (6H, t)
Mass (m/z): 415, 416

EXAMPLE 4
N,N'-Bis[3-carbonyl-1-(2-(2,4-dichlorophenyl)-2-oxoethyl) pyridinium]hydrazine dibromide (Compound 3):
Yield: 24%
m.p.: 225–227° C. (decomp.)
IR(KBr, cm$^{-1}$): 1702, 1666
$^1$H NMR (DMSOd$_6$, 400 MHz) δ: 11.69 (2H,s), 9.58(2H, bs), 9.20–9.18 (4H,m), 8.49–8.47 (2H,m), 8.17–8.15 (2H,d), 7.92 (2H,bs), 7.78–7.76 (2H,d), 6.50 (4H,s)
Mass (m/z): 615, 617, 618, 620.

EXAMPLE 5
1-(2-Ethoxy-2-oxoethyl)-3-(2-(2-pyridyl) hydrazinocarbonyl)pyridinium bromide.hydrochloride (Compound 4):
Yield : 16%
m.p.: 210–212° C.
IR (KBr, cm$^{-1}$): 3140, 3005, 1732 and 1690
$^1$H NMR (DMSOd$_6$, 400 MHz) δ9.63 (1H,s), 9.27 (2H,d), 8.49–8.45 (1H,m) 8.13–8.07 (2H,m), 7.32–7.30 (1H,m), 7.12–7.11 (1H,m), 5.77 (2H,s), 4.23 (2H,q), 1.25 (3H,t)
Mass (m/z): 301, 302

EXAMPLE 6
1-(2-Thien-2'-yl-2-oxoethyl)-3-(methanesulfonyl hydrazinocarbonyl)pyridinium bromide (Compound 5):
Yield: 30%
m.p: 199–200° C.
IR (KBr, cm$^{-1}$): 1714, 1673
$^1$HNMR (DMSOd$_6$, 400 MHz) δ: 11.38 (1H,s), 9.97 (1H,s) 9.51 (1H,s), 9.16 (1H,d), 9.06–9.04 (1H,m), 8.43–8.39 (1H,m), 8.25–8.21 (2H,m), 7.43–7.41 (1H,t), 6.45 (2H,s), 3.08 (3H,s).
Mass (m/z): 340, 341, 342

EXAMPLE 7
N,N'-Bis[3-carbonyl-1-(2-thien-2'-yl-2-oxoethyl) pyridinium]hydrazine dibromide (Compound 6):
Yield: 33%
m.p.: 259–261° C. (decomp.)
IR (KBr, cm$^{-1}$): 3330, 1702, 1674, 1655 and 1626
$^1$H NMR (DMSOd$_6$, 400 MHz) δ: 11.59 (2H,s), 9.50(2H, s), 9.15–9.08 (4H,m), 8.40–8.36 (2H,m), 8.17–8.14 (4H,m), 7.33(2H,t), 6.42 (4H,s)
Mass (m/z): 491, 492.

EXAMPLE 8
1-(2-Ethoxy-2-oxoethyl)-3-(2-(benzoyloxy) ethylaminocarbonyl)pyridinium bromide (Compound 7):
Yield: 85%
m.p.: 132–134° C.
IR (KBr, cm$^{-1}$): 3210, 3067, 1726, 1687, 1656
$^1$H NMR (DMSOd$_6$, 400 MHz) δ: 9.46 (1H,s), 9.37 (1H,t), 9.11(1H,t), 8.97 (1H,d), 8.33–8.29 (1H,m) 7.95–7.93 (2H,m), 7.63–7.59 (1H,m), 7.49–7.45 (2H,m), 5.65 (2H,s), 4.39 (2H,t), 4.19 (2H,q), 3.70–3.69 (2H,m), 1.20 (3H,t)
Mass (m/z): 357, 358, 359

EXAMPLE 9
1-(2-(2,4-Dichlorophenyl)-2-oxoethyl)-3-(2-(benzoyloxy) ethyl aminocarbonyl)pyridinium bromide (Compound 8):
Yield: 75%
m.p.: 102–104° C.
IR(KBr, cm$^{-1}$): 1703, 1685, 1675
$^1$H NMR (DMSOd$_6$, 400 MHz) δ: 9.41–9.37 (2H,m), 9.03–8.98 (2H,m)8.34–8.30 (1H,m), 8.04 (1H,d), 7.91–7.89 (2H,m), 7.82 (1H,d),7.68–7.65 (1H,m), 7.58–7.55 (1H,m), 7.43 (2H,t), 6.35 (2H,s), 4.36 (2H,t), 3.68–3.64 (2H,m)
Mass (m/z): 457, 458, 459, 460, 461, 462

EXAMPLE 10
1-(2-Thien-2'-yl-2-oxoethyl)-3-(2-(2-pyridyl) hydrazinocarbonyl)pyridinium bromide (Compound 9):
Yield: 10%
m.p.: 212–214° C. (decomp)
IR(KBr, cm$^{-1}$): 1685, 1649
$^1$H NMR (DMSOd$_6$, 400 MHz) δ: 11.21 (1H,bs), 9.59 (1H,s), 9.19 (2H,d), 8.44 (1H,t), 8.27–8.24 (2H,m), 8.08 (1H,bs), 7.62 (1H,bs), 7.44 (1H,t), 6.85–6.79 (2H,m), 6.50 (2H,s)
Mass (m/z): 339, 340, 341

EXAMPLE 11
1-(2-Phenyl-2-oxoethyl)-3-(2-(2-pyridyl) hydrazinocarbonyl)pyridinium bromide (Compound 10):
Yield: 4%
m.p.: 190° C. (decomp)
IR(KBr, cm$^{-1}$): 1683, 1670, 1648
$^1$H NMR (DMSOd$_6$, 400 MHz) δ: 11.14 (1H,bs), 9.53 (1H,s), 9.18–9.13 (2H,m), 8.45–8.42 (1H,t), 8.08–8.06 (3H, m), 7.80 (1H,t), 7.67 (2H,t), 7.62–7.55 (1H,m), 6.83–6.76 (2H,m), 6.54 (2H,s)
Mass (m/z): 333, 334, 335

EXAMPLE 12
1-(2-Phenyl-2-oxoethyl)-3-(hydrazinocarbonyl)pyridinium bromide (Compound 11).
Yield: 15%
m.p.: 215–216° C.
IR(KBr, cm$^{-1}$): 1695, 1680
$^1$HNMR (DMSOd$_6$, 400 MHz) δ: 10.25 (1H,s) 9.65 (1H,s), 9.35–9.32 (2H,m), 8.90–8.88 (1H,m) 8.50–8.46 (2H, d), 8.21–8.17 (1H,m), 8.05–8.07 (2H,m), 6.50 (2H,s), 4.45 (2H,s).
Mass (m/z): 256, 257.

EXAMPLE 13
1-(2-Phenyl-2-oxoethyl)-3-(methanesulfonyl hydrazinocarbonyl)pyridinium bromide (Compound 12):
Yield: 35%
m.p.: 227–228° C.
IR(KBr, cm$^{-1}$): 1710, 1702
$^1$HNMR (DMSOd$_6$, 400 MHz) δ: 11.30, (1H,s), 9.88 (1H,s), 9.41 (1H,s), 9.06–9.05 (1H,d) 8.98–8.96 (1H,d), 8.34–8.31 (1H,m), 7.97 (2H,d), 7.72–7.69 (1H,t), 7.59–7.56 (2H,t), 6.44 (2H,s), 2.99 (3H,s)
Mass (m/z): 334, 335

EXAMPLE 14
1-(2-Ethoxy-2-oxoethyl)-3-(methanesulfonyl hydrazinocarbonyl)pyridinium bromide (Compound 13):
Yield: 38%
m.p: 75–76° C.
IR(KBr, cm$^{-1}$): 1739, 1697
$^1$HNMR (DMSOd$_6$, 400 MHz) δ: 11.39 (1H,s), 9.96 (1H,s), 9.56 (1H,s), 9.23 (1H,d), 9.06 (1H,d), 8.40 (1H,t), 5.75 (2H,s), 4.27–4.22 (2H,q), 3:08 (3H,s), 1.26 (3H,t)
Mass (m/z): 301, 302, 303

EXAMPLE 15
1-(2-Phenyl-2-oxoethyl)-3-(phenylsulfonylhydrazino carbonyl)pyridinium bromide (Compound 14):
Yield: 28%
m.p: 187–188° C.(dec.)

IR(KBr, cm$^{-1}$): 1700, 1633
$^1$HNMR (DMSOd$_6$, 400 MHz) δ: 11.38 (1H,s), 10.45 (1H,s), 9.33(1H,s), 9.13–9.12 (1H,d), 8.95 (1H, d), 8.38 (1H,t), 8.05 (2H,d), 7.89 (2H,d), 7.80 (1H,t), 7.66 (3H,t), 7.57 (2H,t), 6.50 (2H,s).
Mass (m/z): 396, 397, 398

EXAMPLE 16

1-(2-Phenyl-2-oxoethyl)-2-chloro-3-(phenylsulfonylhydrazino carbonyl)pyridinium bromide (Compound 15):
Yield: 23%
m.p.: 247–250° C. (decomp)
IR(KBr, cm$^{-1}$): 1685, 1679,
$^1$HNMR (DMSOd$_6$, 400 MHz) δ: 11.12 (1H,s), 9.49 (1H,s), 9.07–9.03(1H,m), 8.44 (1H, t), 8.07 (2H,d), 7.80 (1H,t), 7.67 (2H,t), 7.18 (2H,t), 6.87 (2H,d), 6.77 (1H,t), 6.50 (2H,s).
Mass (m/z): 430, 431, 432

EXAMPLE 17

1-(2-Phenyl-2-oxoethyl)-3-(2-(acetoxy)ethyloxy carbonyl) pyridinium bromide (Compound 16):
Yield: 40%
m.p.: 152–153° C.
IR(KBr, cm$^{-1}$): 1737, 1691, 1635
$^1$HNMR (DMSOd$_6$, 400 MHz) δ: 9.63(1H,s), 9.24(1H,d), 9.12(1H,d), 8.43(1H,t), 8.07(2H,d), 7.80(1H,t), 7.67(2H,t), 6.59(2H,s), 4.62–4.60 (2H,m), 4.39–4.37(2H,m), 2.03 (3H, s)
Mass (m/z): 328, 329

EXAMPLE 18

1-(2-Ethoxy-2-oxoethyl)-3-(2-(benzoyloxy) ethyloxycarbonyl)pyridinium bromide (Compound 17):
Yield: 35%
m.p.: 142–143° C.
IR(KBr, cm$^{-1}$): 1736, 1718, 1636
$^1$HNMR (DMSOd$_6$, 400 MHz) δ: 9.60(1H,s), 9.20–9.18 (1H,d), 9.04–9.02(1H,d), 8.33–8.29(1H,m), 7.90–7.88(2H, d), 7.58–7.57(1H,m), 7.46–7.42(2H,m), 5.67(2H,s), 4.71–4.68(2H,m), 4.58–4.56(2H,m), 4.15(2H,q), 1.16(3H,t)
Mass (m/z): 358, 359, 360

EXAMPLE 19

1-(2-Thien-2'-yl-2-oxoethyl)-4-(2-(benzoyloxy) ethylaminocarbonyl)pyridinium bromide (Compound 18):
m.p.: 210–211° C.
IR(KBr, cm$^{-1}$): 1723, 1680, 1668
$^1$HNMR (DMSOd$_6$, 400 MHz) δ: 9.52 (1H,t), 9.14 (2H, d), 8.50 (2H,d), 8.25–8.21 (2H,m), 8.01–7.99 (2H,d), 7.67 (1H,t), 7.55–7.51 (2H,m), 7.42–7.40 (1H,m), 6.42 (1H,s) 4.47–4.45 (2H,t), 3.77–3.73 (2H, m).
Mass (m/z): 395, 396

EXAMPLE 20

1-(2-Ethoxy-2-oxoethyl)-4-(phenylsulfonyl hydrazino carbonyl)pyridinium bromide (Compound 19):
Yield: 60%
m.p.: 171–173° C.
IR (KBr, cm$^{-1}$): 1745, 1685, 1645.
$^1$HNMR (DMSOd$_6$, 400 MHz) δ: 11.41 (1H, s), 10.39 (1H, s), 9.10 (2H, d), 8.27 (2H, d), 7.82–7.80 (2H, d), 7.60–7.57 (1H, t), 7.50–7.46 (2H, t), 5.63 (2H, s), 4.18–4.12 (2H, q), 1.19–1.15 (3H, t).
Mass (m/z): 364, 365, 366

EXAMPLE 21

1-(2-Phenylamino-2-oxoethyl)-4-(phenylsulfonyl hydrazino carbonyl)pyridinium chloride (Compound 20):
Yield: 10%
m.p.: 225–227° C.
IR (KBr, cm$^{-1}$): 1693, 1642, 1592
$^1$HNMR(DMSOd$_6$, 400 MHz) δ: 11.55 (1H,s), 10.99 (1H, s), 10.49 (1H,s), 9.20 (2H,d), 8.34 (2H,d), 7.89 (2H,d), 7.73–7.64 (1H,t), 7.61–7.56 (4H, m), 7.37–7.33 (2H,t), 7.12–7.09 (1H,t), 5.73 (2H,s).
Mass (m/z): 411, 412, 413, 414

EXAMPLE 22

1-(2-Ethoxy-2-oxoethyl)-3-(phenylsulfonylhydrazino carbonyl)pyridinium bromide (Compound 21):
Yield: 75%
m.p.: 145–147° C.
IR(KBr cm$^{-1}$): 1744, 1713, 1633
$^1$HNMR (DMSOd$_6$, 400 MHz) δ: 11.27(1H,s),10.36 (1H, s), 9.28(1H,s), 9.09(1H,d), 8.83(1H,d),8.27–8.24 (1H,m), 7.82–7.79 (2H,m), 7.58 (1H,t), 7.48 (2H, t), 5.59 (2H, s), 4.17–4.12 (2H, q), 1.16(3H,t).
Mass (m/z): 364, 365, 366

EXAMPLE 23

1-(2-(2,4-Dichlorophenyl)-2-oxoethyl)-3-(2(methoxy) ethyloxycarbonyl)pyridinium bromide (Compound 22):
Yield: 25%
m.p.: 156–158° C.
IR(KBr, cm$^{-1}$): 1731, 1706, 1640
$^1$HNMR (DMSOd$_6$, 400 MHz) δ: 9.61 (1H, s), 9.20 (1H, d), 9.13 (1H, d), 8.45–8.41 (1H, m), 8.15 (1H, d), 7.92(1H, d), 7.78–7.76 (1H, m), 6.49 (2H, s), 4.56–4.54 (2H, m), 3.72–3.69 (2H, q), 3.31 (3H, s).
Mass (m/z): 368, 369, 370, 371

EXAMPLE 24

1-(2-Phenylamino-2-oxoethyl)-3-(2-(benzoyloxyl) ethylaminocarbonyl)pyridinium chloride (Compound 23):
Yield: 70%
m.p.: 171–172° C.
IR (KBr, cm$^{-1}$): 1720, 1692, 1668
$^1$HNMR: (DMSOd$_6$, 400 MHz) δ: 11.06 (1H, s), 9.67 (1H, t), 9.59 (1H, s), 9.20 (1H,d), 9.11 (1H, d), 8.36–8.32 (1H, m), 8.00 (2H, d), 7.66–7.61 (3H, m), 7.51 (2H, t), 7.34 (2H, t), 7.10 (1H, t), 5.77 (2H,s), 4.45 (2H, t), 3.76–3.72 (2H, q).
Mass (m/z): 404, 405, 406, 407

EXAMPLE 25

1-(2-Thien-2'-yl-2-oxoethyl)-3-(phenylaminocarbonyl hydrazinocarbonyl)pyridinium bromide (Compound 24):
Yield: 30%
m.p.: 202–204° C.
IR(KBr, cm$^{-1}$): 1718, 1673
$^1$HNMR: (DMSOd$_6$, 400 MHz) δ: 11.03 (1H, s), 9.55 (1H, s), 9.18 (1H, d), 9.10 (1H, d), 9.00 (1H, s),8.57 (1H,s), 8.46–8.42 (1H, t), 8.25–8.22 (2H, m), 7.47–7.45 (2H, d), 7.43–7.41 (1H, t), 7.29–7.25 (2H, t), 7.0–6.96 (1H, t), 6.46 (2H, s).
Mass (m/z): 381, 382, 383

EXAMPLE 26

1-(2-Phenyl-2-oxoethyl)-3-(2-(acetoxy) ethylaminocarbonyl)pyridinium bromide (Compound 25):
Yield: 55%
m.p.: 186–188
IR (KBr, cm$^{-1}$): 1734, 1697, 1679

$^1$HNMR (DMSOd$_6$, 400 MHz) δ: 9.47(1H,s), 9.36 (1H,t), 9.13–9.05 (2H, m), 8.42–8.38 (1H, m), 8.06 (2H, d), 7.80 (1H, t), 7.67 (2H, t), 6.54(2H, s), 4.18 (2H,t), 3.61–3.57 (2H,q), 2.02 (3H,s).

Mass (m/z): 327, 328, 329.

EXAMPLE 27

1-(2-Phenylamino-2-oxoethyl)-3-(phenyl sulfonyl hydrazino carbonyl)pyridinium chloride (Compound 26):

Yield: 38% m.p.: 232–234° C.

IR (KBr, cm$^{-1}$): 1689, 1636, 1596

$^1$HNMR (DMSOd$_6$, 400 MHz) δ: 11.30 (1H, s), 10.80 (1H, s), 10.37 (1H, s), 9.29 (1H, s), 9.09 (1H, d), 8.81 (1H, d), 8.25–8.21 (1H, t), 7.82–7.80 (2H,d), 7.59–7.46 (5H, m), 7.28–7.24 (2H, t), 7.04–7.00 (1H, t), 5.62 (2H,s).

Mass (m/z): 411, 412, 413, 414

EXAMPLE 28

1-(2-Phenylamino-2-oxoethyl)-3-((4-methylphenyl) sulfonyl hydrazino carbonyl)pyridinium chloride (Compound 27):

Yield: 48% m.p.: 205–206° C.

IR(KBr, cm$^{-1}$): 1712, 1681, 1632

$^1$HNMR (DMSOd$_6$, 400 MHz) δ: 11.35 (1H, s), 10.86 (1H, s), 10.36 (1H, s), 9.38 (1H, s), 9.17 (1H, d), 8.90 (1H,d), 8.34–8.30 (1H, m), 7.78-(2H,d), 7.59 (2H, d), 7.37–7.33 (4H,m), 7.11 (1H,t), 5.70 (2H,s), 2.36 (3H, s).

Mass (m/z): 425, 426, 427, 428

EXAMPLE 29

1-(2-Phenyl-2-oxoethyl)-3-(2-(benzoyloxy)ethyloxy carbonyl)pyridinium bromide (Compound 28):

Yield: 35% m.p.: 132–134° C.

IR (KBr, cm$^{-1}$): 1730, 1705, 1690

$^1$HNMR (DMSOd$_6$, 400 MHz) δ: 9.80 (1H, s), 9.36 (1H, d), 9.30 (1H, d), 8.58 (1H, t), 8.21 (2H, d), 8.12 (2H, d), 7.95 (1H, t), 7.85–7.80(3H, m), 7.68 (2H, t), 6.71 (2H, s), 4.95–4.93 (2H, m), 4.82–4.80 (2H, m).

Mass (m/z): 390, 391, 392.

EXAMPLE 30

1-(2-Thien-2'-yl-2-oxoethyl)-3-(phenylcarbonyl hydrazino carbonyl)pyridinium bromide (Compound 29):

Yield: 45% m.p.: 80–81° C.

IR(KBr Cm$^{-1}$): 1700, 1663, 1631

$^1$HNMR (DMSOd$_6$, 400 MHz) δ: 11.49 (1H, s), 10.95 (1H, s), 9.67 (1H, s), 9.34 (1H, d), 9.27 (1H, d), 8.52–8.48 (1H, m), 8.29–8.28 (2H, m), 8.00 (2H, d), 7.68 (1H, t), 7.59 (2H, t), 7.46 (1H, t), 6.63 (2H,s)

Mass (m/z): 366, 367, 368, 369

EXAMPLE 31

1-(2-Ethoxy-2-oxoethyl)-3-((phenylmethyl)sulfonyl hydrazino carbonyl)pyridinium bromide (Compound 30):

Yield: 50% m.p.: 147–148° C.

IR (KBr, cm$^{-1}$): 1749, 1698, 1640

$^1$HNMR (DMSOd$_6$, 400 MHz) δ: 11.57 (1H, s), 10.21 (1H,s), 9.75 (1H,s), 9.38 (1H, d), 9.24 (1H, d), 8.59–8.56 (1H, m), 7.67–7.65 (2H, m), 7.58–7.52 (3H, m), 5.90 (2H, s), 4.68 (2H, s), 4.45–4.39 (2H, q), 1.43 (3H, t).

Mass (m/z): 377, 378, 379

EXAMPLE 32

1-(2-Phenyl-2-oxoethyl)-3-((phenylmethyl)sulfonyl hydrazino carbonyl)pyridinium bromide (Compound 31):

Yield: 80% m.p.: 205–207° C.

IR (KBr, Cm$^{-1}$): 1687, 1637

$^1$HNMR (DMSOd$_6$, 400 MHz) δ: 11.59 (1H,s), 10.20 (1H,s), 9.71 (1H,s), 9.33 (1H, d), 9.27 (1H, d), 8.62–8.59 (1H, m), 8.25–8.23 (2H, d), 7.99–7.95 (11H, t), 7.86–7.82 (2H, t), 7.67–7.65 (2H, m), 7.57–7.52 (3H, m),6.72 (2H, s), 4.69 (2H, s).

Mass (m/z): 410, 411, 412, 413

Pharmaceutical Compositions

Pharmaceutical compositions may be prepared with a pharmaceutically effective quantity of compounds of general formula I, individually or in combination. The following pharmaceutical formulations suggested are by way of example alone and in no way restrict the forms in which they can be used.

Oral Formulations

Oral formulations may be administered as solid dosage forms for example pellets, powders, sachets or discreet units such as tablets or capsules and like. Other orally administered pharmaceutical preparations include monophasic and biphasic liquid dosage forms either in ready to use form or forms suitable for reconstitution such as mixtures, syrups, suspensions or emulsions. The preparations in addition may contain diluents, dispersing agents, buffers, stabilizers, solubilizers, surfactants, preservatives, chelating agents and/or other pharmaceutical additives as are used. Aqueous or non aqueous vehicle or their combination may be used and if desired may contain suitable sweetener, flavoring agent or similar substances. In case of suspension or emulsion a suitable thickening agent or suspending agent or emulsifying agent may be present in addition. Alternatively, the compounds may be administered as such in their pure form unassociated with other additives for example as capsules or sachets. It may also be administered with a vehicle. Pharmaceutical preparations can have a slow, delayed or controlled release of active ingredients as is provided by a matrix or diffusion controlled system.

When the present invention or its salts or suitable complexes is presented as a discreet unit dosage form like tablet, it may contain in addition medically inert excipients as are used in the art. Diluents such as starch, lactose, dicalcium phosphate, talc, magnesium stearate, polymeric substances like methyl cellulose, fatty acids and derivatives, sodium starch glycollate, etc. may also be used.

EXAMPLE 33

Preparation of Oral Dosage Form

A typical tablet has the following composition:

| | |
|---|---|
| Active ingredient of formula I | as given above |
| Lactose | 135 mg |
| Starch | 76 mg |
| Polyvinyl pyrolidone (K-30) | 2 mg |
| Talc | 1.5 mg |
| Magnesium Stearate | 1.0 mg |

Parenteral Formulations

For parenteral administration, the compounds or their salts or suitable complexes thereof may be present in a sterile vehicle which may be an aqueous or non aqueous vehicle or a combination thereof. The examples of vehicles are water, ethyl oleate, oils and derivatives of polyols, glycols and their derivatives. It may contain additives common in injectable preparations like stabilizers, solubilizers, pH modifiers, buffers, antioxidants, cosolvents, complexing agents, tonicity modifiers, etc.

Some suitable additives are for example tartrate, citrate or similar buffers, alcohol, sodium chloride, dextrose and high molecular weight polymers. Another alternative is sterile powder reconstitution. The compound may be administered in the form of injection for more than once daily administration, or intravenous infusion/drip or suitable depot preparation.

EXAMPLE 34

Preparation Suitable for Parenteral Administration has the Following Composition

| Active ingredient of formula I | as given above |
|---|---|
| Polyethylene glycol (400) | 0.75 ml |
| Sodium metabisulphite | 0.01% |
| Isotonic saline/WFI | q.s. |

Other Formulations

For the dermatological application and for the discoloration of teeth, the recommended formulations are lotions, oral rinse and toothpaste containing appropriate amount of the compounds of the general formula I.

The above examples are presented by way of illustration alone and in no way limit the scope of the invention.

I claim:

1. A compound represented by formula (I) or a pharmaceutically acceptable salt thereof:

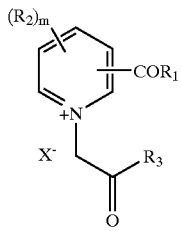

(I)

wherein $R_1$ is —$R_4$–$R_5$ or $R_{11}$, $R_{11}$ is selected from the group consisting of NHNH—(2-pyridyl), —NHNHCONHPh, —NHNHCOPh, structure

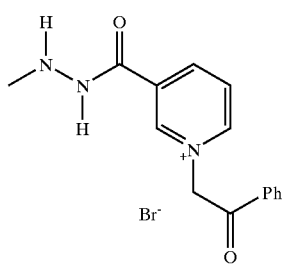

(a)

or

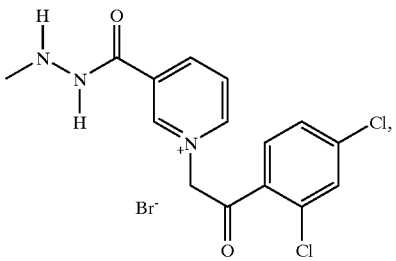

(c)

$R_4$ is selected from the group consisting of —N($R_7$) $R_6$O—, —N($R_7$)$R_6$N($R_7$), —O$R_6$O, and —O$R_6$N($R_7$)—, where $R_6$ is alkyl having 2 to 8 carbon atoms;

$R_5$ is selected from the group consisting of alkyl, aryl containing up to two conjugated or fused ring systems including heteroaryl,

—CO$R_7$, —SO$_2$$R_7$, —C(S)NHR$_7$, —C(NH)NHR$_7$, —COR$_{10}$,

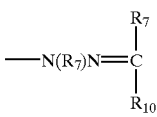

where $R_7$ is selected from the group consisting of H, alkyl and aryl containing up to two conjugated or fused ring systems including heteroaryl, provided $R_7$ might be different for $R_1$ and $R_3$ in the same compound; $R_2$ is selected from the group consisting of F, Cl, Br, I, O$R_7$, NO$_2$, alkyl, aryl containing up to two conjugated or fused ring systems including heteroaryl, formyl, acyl, C(O)NR$_7$R$_{10}$, C(O)OR$_7$, NR$_7$R$_{10}$, N=C(R$_7$)(R$_{10}$), SR$_7$, SO$_2$NH$_2$, SO$_2$ alkyl and SO$_2$ aryl; m is 0, 1 or 2;

$R_3$ is selected from the group consisting of $R_7$, O$R_7$, N($R_7$) ($R_{10}$), N=C($R_7$) ($R_{10}$), N($R_7$) N($R_7$) ($R_{10}$), N($R_7$) N=C($R_7$) ($R_{10}$) and CH($R_7$)C(O)$R_8$ where $R_8$ is selected from the group consisting of $R_7$, O$R_7$ and NR$_7$R$_{10}$;

$R_{10}$ is selected from the group consisting of H, alkyl and aryl containing up to two conjugated or fused ring systems including heteroaryl and in each case optionally different from substituent $R_7$, provided $R_{10}$ might be different for $R_1$ and $R_3$ in the same compound;

X is selected from the group consisting of a halide ion, acetate ion, perchlorate ion, sulfonate ion, oxalate ion. citrate ion, tosylate ion, maleate ion, mesylate ion, carbonate ion, sulfite ion, phosphoric hydrogen ion, phosphonate ion, phosphate ion, BF$_4$- and PF$_6$-;

with proviso that, (i) when two alkyl groups are present on the same carbon or nitrogen, they are optionally linked together to form a cyclic structure and (ii) the nitrogen of heteroaryl ring of $R_{10}$, when present, is optionally quaternized.

2. The compound as claimed in claim 1, which is selected from the group consisting of the following compounds:

(a) N,N'-bis[3-carbonyl-1-(2-thien-2'-yl-2-oxoethyl)-3-pyridinium]hydrazine dibromide or a pharmaceutically acceptable salt thereof, (c) 1-(2-ethoxy-2-oxoethyl)-3-(2-(benzoyloxy)ethylamino carbonyl)pyridinium bromide or a pharmaceutically acceptable salt thereof, (l) 1-(2-thien-2'-yl-2-oxoethyl)-4-(2-(benzolyloxy)ethyl aminocarbonyl)pyridinium bromide or a pharmaceutically acceptable salt thereof, (m) 1-(2-(2,4-dichlorophenyl)-2-oxoethyl)-3-(2-(benzoyloxy)ethylaminocarbonyl)pyridinium bromide or a pharmaceutically acceptable salt thereof, (n) 1-(2-phenyl-2-oxoethyl)-3-(2-(acetoxy)ethyloxy) carbonyl)pyridinium bromide or a pharmaceutically acceptable salt thereof, (o) 1-(2-ethoxy-2-oxoethyl)-3-(2-(benzoyloxy)ethyloxy carbonyl)pyridinium bromide or a pharmaceutically acceptable salt thereof, (q) 1-(2-(2,4-dichlorophenyl)-2-oxoethyl)-3-(2(methoxy) ethyloxycarbonyl)pyridinium bromide or a pharmaceutically acceptable salt thereof, (r) 1-(2-phenylamino-2-oxoethyl)-3-((benzoyloxy) ethylaminocarbonyl)pyridinium chloride or a pharmaceutically acceptable salt thereof, (t) 1-(2-phenyl-2-oxoethyl)-3-(2-(acetoxy) ethylaminocarbonyl)pyridinium bromide or a pharmaceutically acceptable salt thereof, and (w) 1-(2-phenyl-2-oxoethyl)-3-(2-(benzoyloxy)ethyloxy carbonyl)pyridinium bromide or a pharmaceutically acceptable salt thereof.

3. A method of treating complications in a diabetic patient by breaking a preformed AGE, within said patient, which comprises, administering an effective amount of a compound represented by formula (I), as claimed in claim 1, either singly, or in combination with other drugs for antidiabetic therapy.

4. A method of preventing or treating diseases caused by diabetes and aging related complications, which comprises, administering to a patient in need thereof, an effective amount of a compound represented by formula (I), as claimed in claim 1, either singly or in combination with a pharmaceutically acceptable carrier, diluent or excipient, wherein the disease prevented or treated is a kidney disease, nerve damage, atherosclerosis, retinopathy, dermatological disorder or a non-enzymatic browning of oral cavity.

5. A process for the preparation of the compound as claimed in claim 1, which comprises preparing a substituted pyridine, according to the desired end product followed by quaternizing of the substituted pyridine, with an appropriate reagent by refluxing in an alcoholic and/or high boiling solvent for 6–48 hours to give the desired compound.

6. A pharmaceutical composition which comprises a pharmaceutically effective amount of one or more of the compounds defined in claim 1, in admixture with a pharmaceutically acceptable carrier, diluent, solvent or excipient.

7. The pharmaceutical composition as claimed in claim 6, in the form of an oral formulation.

8. The pharmaceutical composition as claimed in claim 6, wherein said pharmaceutically acceptable carrier is selected from the group consisting of starch, lactose, polyvinyl pyrrolidone (K-30), talc and magnesium stearate.

9. The pharmaceutical composition as claimed in claim 6, in the form of a parenteral formulation.

10. A method for the preparation of a parenteral formulation, which comprises dissolving one or more compounds defined in claim 1, in polyethylene glycol 400 and diluting the solution so obtained, with an isotonic solution or water to a desired concentration.

11. The pharmaceutical composition as claimed in claim 6, in the form of a lotion, oral rinse or toothpaste.

12. The compound as claimed in claim 1, wherein said aryl group represented by $R_5$, $R_7$, $R_2$, and $R_{10}$, which may be substituted or unsubstituted, is selected from the group consisting of phenyl, pyridyl and thienyl.

13. The compound as claimed in claim 1, wherein said heteroaryl group represented by $R_5$, $R_7$, $R_2$, and $R_{10}$ has a hetero atom selected from the group consisting of sulfur, nitrogen and oxygen.

14. Compounds:

(b) 1-(2-ethoxy-2-oxoethyl)-3-(2-(2-pyridyl) hydrazinocarbonyl)pyridinium bromide.hydrochloride or a pharmaceutically acceptable salt thereof, (d) N,N'-bis[3-carbonyl-1-(2-phenyl-2-oxoethyl) pyridinium]hydrazine dibromide or a pharmaceutically acceptable salt thereof, (g) N,N'-bis[3-carbonyl-1-(2-(2,4-dichlorophenyl)-2-oxoethyl)pyridinium]hydrazine dibromide or a pharmaceutically acceptable salt thereof, (s) 1-(2-thien-2'-yl-2-oxoethyl)-3-(phenylaminocarbonyl hydrazinocarbonyl)pyridinium bromide or a pharmaceutically acceptable salt thereof, and (x) 1-(2-thien-2'-yl-2-oxoethyl)-3-(phenylcarbonyl hydrazino carbonyl)pyridinium bromide or a pharmaceutically acceptable salt thereof.

15. A method of treating complications in a diabetic patient by breaking a preformed AGE, within said patient, which comprises, administering an effective amount of one or more of compounds (b), (d), (g), (s) or (x), as claimed in claim 14, either singly, or in combination with other drugs for antidiabetic therapy.

16. A method of preventing or treating diseases caused by diabetes and aging related complications, which comprises, administering to a patient in need thereof, an effective amount of one or more of compounds (b), (d), (g), (s) or (x), as claimed in claim 14, either singly or in combination with a pharmaceutically acceptable carrier, diluent or excipient, wherein the disease prevented or treated is a kidney disease, nerve damage, atherosclerosis, retinopathy, dermatological disorder or a non-enzymatic browning of oral cavity.

17. A process for the preparation of compound (b), (d), (g), (s) or (x), as claimed in claim 14, which comprises preparing a substituted pyridine, according to the desired end product followed by quaternizing of the substituted pyridine, with an appropriate reagent by refluxing in an alcoholic and/or high boiling solvent for 6–48 hours to give the desired compound.

18. A pharmaceutical composition which comprises a pharmaceutically effective amount of one or more of compounds (b), (d), (g), (s) or (x), as claimed in claim 14, in admixture with a pharmaceutically acceptable carrier, diluent, solvent or excipient.

19. The pharmaceutical composition as claimed in claim 18, in the form of an oral formulation.

20. The pharmaceutical composition as claimed in claim 18, wherein said pharmaceutically acceptable carrier is selected from the group consisting of starch, lactose, polyvinyl pyrrolidone (K-30), talc and magnesium stearate.

21. The pharmaceutical composition as claimed in claim 18, in the form of a parenteral formulation.

22. A method for the preparation of a parenteral formulation, which comprises dissolving one or more of compounds (b), (d), (g), (s) and (x), as claimed in claim 14, in polyethylene glycol 400 and diluting the solution so obtained, with an isotonic solution or water to a desired concentration.

23. The pharmaceutical composition as claimed in claim 18, in the form of a lotion, oral rinse or toothpaste.

UNITED STATES PATENT AND TRADEMARK OFFICE
CERTIFICATE OF CORRECTION

PATENT NO.   : 6,624,178 B2
DATED        : September 23, 2003
INVENTOR(S)  : Alangudi Sankaranarayanan It is certified that error appears in the above-identified patent and that said Letters Patent is hereby corrected as shown below:

Column 5,
Line 35, Table 1A, heading -X, Compound 4, delete "Br" and insert -- Br·HCl --.

Signed and Sealed this

Twenty-seventh Day of April, 2004

JON W. DUDAS
*Acting Director of the United States Patent and Trademark Office*